United States Patent
Satoji et al.

(10) Patent No.: US 8,002,471 B2
(45) Date of Patent: Aug. 23, 2011

(54) FLUID DYNAMIC BEARING APPARATUS AND A MOTOR USING THE SAME

(75) Inventors: Fuminori Satoji, Kuwana (JP); Ryouichi Nakajima, Kuwana (JP); Isao Komori, Kuwana (JP); Kazuo Okamura, Kuwana (JP); Masafumi Okuma, Tokyo (JP); Kenichi Mitani, Tokyo (JP)

(73) Assignee: NTN Corporation, Osaka-fu (JP)

( * ) Notice: Subject to any disclaimer, the term of this patent is extended or adjusted under 35 U.S.C. 154(b) by 0 days.

(21) Appl. No.: 12/754,100

(22) Filed: Apr. 5, 2010

(65) Prior Publication Data

US 2010/0194215 A1 Aug. 5, 2010

Related U.S. Application Data

(62) Division of application No. 11/587,535, filed as application No. PCT/JP2005/008891 on May 16, 2005, now Pat. No. 7,819,585.

(30) Foreign Application Priority Data

May 25, 2004 (JP) ................................. 2004-155219
May 25, 2004 (JP) ................................. 2004-155230

(51) Int. Cl.
*F16C 32/06* (2006.01)
(52) U.S. Cl. ........................ 384/100; 384/107
(58) Field of Classification Search .................. 384/100, 384/107, 114, 121; 310/90; 360/99.08, 98.07; 417/354, 423.12, 423.13
See application file for complete search history.

(56) References Cited

U.S. PATENT DOCUMENTS

| 5,363,003 | A | * | 11/1994 | Harada et al. | .................. 310/91 |
| 5,436,519 | A | * | 7/1995 | Takahashi et al. | .............. 310/90 |
| 5,683,183 | A | * | 11/1997 | Tanaka et al. | ................. 384/100 |
| 6,380,651 | B1 | * | 4/2002 | Yamaguchi et al. | ............ 310/90 |

(Continued)

FOREIGN PATENT DOCUMENTS

JP 63-59757 3/1988

(Continued)

OTHER PUBLICATIONS

Office Action issued Sep. 14, 2010 in corresponding Japanese Application No. 2004-155219 (with partial English translation).

(Continued)

*Primary Examiner* — Thomas R Hannon
(74) *Attorney, Agent, or Firm* — Wenderoth, Lind & Ponack, L.L.P.

(57) ABSTRACT

Assembly precision in a motor is improved and greater cost reduction is achieved.
A fluid dynamic bearing apparatus 1 comprising a housing 7 and bearing sleeve 8 as fixed-side members 2, a shaft member 9 as a rotational-side member 3 having a portion 3c for mounting a rotor magnet 5, and a disk hub 10, the shaft member 9 being supported by the bearing sleeve 8 in the radial direction in a non-contact manner by the hydrodynamic effect of a lubricating oil produced in a radial bearing gap between the inner circumferential surface 8a of the bearing sleeve 8 and the outer circumferential surface 9a of the shaft member while the shaft member 9 is in rotation, the apparatus 1 comprising a disk hub 10 which is fixed on the shaft member 9 and has a portion 3c for mounting the rotor magnet 5, and the disk hub 10 being a molded resin article formed by insert-molding using the shaft member 9 as an insert piece.

12 Claims, 5 Drawing Sheets

U.S. PATENT DOCUMENTS

| | | |
|---|---|---|
| 6,765,326 B1 * | 7/2004 | Nakazono et al. ............. 310/90 |
| 6,768,236 B2 * | 7/2004 | Tokunaga et al. ............. 310/90 |
| 7,086,843 B2 * | 8/2006 | Cheng ....................... 417/423.1 |
| 2002/0018603 A1 * | 2/2002 | Narita ........................... 384/100 |
| 2004/0008912 A1 | 1/2004 | Gomyo et al. |
| 2005/0117822 A1 * | 6/2005 | Chen et al. ................... 384/100 |

FOREIGN PATENT DOCUMENTS

| | | |
|---|---|---|
| JP | 2-139474 | 11/1990 |
| JP | 8-186970 | 7/1996 |
| JP | 10-215548 | 8/1998 |
| JP | 2003-189522 | 7/2003 |
| JP | 2003-329032 | 11/2003 |
| JP | 2004-92814 | 3/2004 |

OTHER PUBLICATIONS

International Search Report issued Jun. 14, 2005 in corresponding International Application No. PCT/JP2005/008891.

* cited by examiner

FLUID DYNAMIC BEARING APPARATUS AND A MOTOR USING THE SAME

This application is a divisional of application Ser. No. 11/587,535, filed Jul. 12, 2007, now U.S. Pat. No. 7,819,585 which is the National Stage of International Application No. PCT/JP2005/008891, filed May 16, 2005.

FIELD OF THE INVENTION

The present invention relates to a fluid dynamic bearing apparatus which supports a shaft member by the hydrodynamic effect of a fluid which is produced in a radial bearing gap in a non-contact manner.

This fluid dynamic bearing apparatus is for use in spindle motors for disk apparatuses, polygon scanner motors for laser beam printers (LBP) and in other small motors. Enhanced speed, cost reduction, noise reduction, etc., as well as high rotational accuracy, are required for these motors. One of the components which determine these required performances is a bearing which supports the spindles of said motors. In recent years, the use of fluid dynamic bearings having excellent characteristics in terms of the required performances mentioned above has been studied or actually started.

For example, for a spindle motor of a disk drive unit such as HDD, a fluid dynamic bearing apparatus which comprises a radial bearing portion which supports a shaft member in the radial direction in a non-contact manner and a thrust bearing portion which supports the shaft member in the thrust direction in a non-contact manner is used. At this time, hydrodynamic grooves are provided as a hydrodynamic pressure producing means on the inner circumferential surface of a bearing sleeve which forms the radial bearing portion or on the outer circumferential surface of the shaft member. Moreover, the hydrodynamic grooves are also provided on both end faces of a flange portion of the shaft member which forms the thrust bearing portion or on the faces opposing these (end faces of the bearing sleeve, end faces of a thrust plate fixed on a housing, etc.) (for example, refer to Japanese Unexamined Patent Publication No. 2000-291648).

SUMMARY OF THE INVENTION

The spindle motor mentioned above is constituted of such a fluid dynamic bearing apparatus and many other parts such as a stator coil, rotor magnet and disk hub. To ensure high rotational performance required for the increasingly high performance of information appliances, efforts to improve the processing precision and assembly precision of each part have been made. Meanwhile, a demand for cost reduction in this type of motors is increasing.

Therefore, an object of the present invention is to improve assembly precision in a motor, as well as to achieve further cost reduction.

To solve the object mentioned above, a fluid dynamic bearing apparatus according to the present invention comprises a fixed-side member and a rotational-side member, supports the rotational-side member by the hydrodynamic effect of a fluid which is produced in an annular radial bearing gap between the fixed-side member and the rotational-side member in the radial direction in a non-contact manner, the rotational-side member having a portion for mounting a rotor magnet and being an injection-molded article of a resin using a metal part as an insert piece. The rotational-side member herein comprises at least a member having a portion for mounting a rotor magnet and a metal part. The portion for mounting a rotor magnet may be composed of the metal part.

The metal part may have any shape or function, and comprises parts which are essential for its bearing function, or parts added to improve its bearing function. Examples of the "member having a portion for mounting a rotor magnet" include disk hubs and turntables for supporting magnetic disks and like disks and rotor components for attaching polygon mirrors, among others.

Forming the rotational-side member of a resin material enables a greater reduction in weight than forming a metal by machining or like means, and it also allows production at a low cost. In particular, reduction in the weight of the rotational-side member allows rapid start and stop of the motor. Moreover, by injection-molding the rotational-side member using a metal part as an insert piece, the trouble of additionally mounting the disk hub or like member and the metal part in a later process step can be saved. The cost of assembling the motor can be thus reduced. Furthermore, the mounting precision between the disk hub or like members and metal part can be improved, and sufficient fixing force can be also ensured between them. Generally, the inaccuracies of the rotational-side member can greatly affect the bearing performance, for example, it can be a cause for shaft runout or other problems. According to the present invention, lowered bearing performance resulting from inaccuracies in mounting can be avoided.

Examples of metal parts which are insert-molded integrally with the rotational-side member include the shaft member facing the radial bearing gap. According to this, the disk hub, turntable, rotor member and like parts which are originally components of the motor which are originally components of the motor can be integrated into the fluid dynamic bearing apparatus together with the shaft member to form an assembly as a component of the fluid dynamic bearing apparatus. Therefore, in the assembly step of the motor, the operation of mounting of these components on the shaft member can be dispensed with, and the cost of assembling the motor can be reduced. The shaft member as a metal part is not necessarily entirely formed of a metal. For example, the hollow portion of a cylindrical metallic material can be filled with a resin during insert molding, whereby the shaft member can be a composite article of a metal and a resin.

Moreover, another example of metal parts which is insert-molded integrally with the rotational-side member is a core.

As mentioned above, when the rotational-side member is molded of a resin material, the greater the thickness of the member, the greater the amount of the shrinkage and the dimensional change caused by a change in temperature during use. Since in the present invention, the rotational-side member is injection-molded of a resin material with a core made of metal as an insert piece and part of the resin portion is replaced by the core, reduction in the weight of the rotational-side member and in the production cost can be achieved, and at the same the dimensional change during molding and during use can be reduced to increase the dimensional accuracy of the rotational-side member. The core can be installed throughout the entire rotational-side member, or it can be partially installed only in a region where the amount of the dimensional change of the resin is large. From a perspective of minimizing the amount of dimensional change, it is desirable that the core is embedded in the rotational-side member. However, part of it may be exposed over the rotational-side member if it causes no problem.

The core can be formed of, for example, a magnetic substance. According to this, the leakage of magnetic flux produced between the stator coil and rotor magnet through the rotational-side member can be prevented.

The core can also be formed of, for example, a porous body such as a sintered metal. According to this, the anchor effect produced in the surface opening of the porous body makes the resin portion covering the core to grip well on the core and resin portion and increases the sticking strength of the core.

Moreover, to solve the object mentioned above, the fluid dynamic bearing apparatus according to the present invention comprises a shaft member, a fixed-side member which freely rotatably supports the shaft member, a member which is attached to the shaft member and has a portion for mounting a rotor magnet, the shaft member being supported in the radial direction in a non-contact manner by the hydrodynamic effect of a fluid which is produced in an annular radial bearing gap between the fixed-side member and the shaft member, the member having a portion for mounting a rotor magnet being molded of a resin, and in this member having a portion for mounting a rotor magnet, a magnetic shielding member comprising a magnetic substance being disposed at least in a portion which opposes the rotor magnet.

Molding the member having a portion for mounting a rotor magnet of a resin material enables weight reduction greater than in a component molded of metal by machining or other means and production at a low cost. In particular, the reduction of the weight of the member having a portion for mounting a rotor magnet allows rapid start and stop of the motor. When the member having a portion for mounting a rotor magnet is made of a resin as stated above, the magnetic flux produced between the stator coil and rotor magnet may leak through the member having the mounting portion to cause magnetic force loss. In the member having a portion for mounting a rotor magnet, however, a magnetic shielding member comprising the magnetic substance at least in the portion opposing the rotor magnet can be disposed to prevent such leakage of magnetic flux and improve the rotational performance of the motor.

By making the member having a portion for mounting a rotor magnet an injection-molded article of a resin using the magnetic shielding member as an insert piece, the trouble of additionally mounting the disk hub and like members and magnetic shielding member in later process steps can be saved, and the cost of assembling the motor can be reduced. The member having a portion for mounting a rotor magnet can be also injection-molded of a resin material using the magnetic shielding member and shaft member as insert pieces, whereby a further reduction in assembling cost can be achieved.

In insert molding, it is desirable that the magnetic shielding member is at least partially embedded in the resin portion of the member having a portion for mounting a rotor magnet. This causes the regions in the resin portion covering the embedded portion of the magnetic shielding member opposing each other to shrink in the direction that clamps the magnetic shielding member when cured. Therefore, the fixing force between the resin portion and magnetic shielding member can be further increased.

Various substances are usable as materials for the aforementioned magnetic shielding member insofar as the substance exhibits a magnetic property. For example, metallic materials including stainless steel and their oxides, ceramics and the like can be suitably used. Moreover, when the magnetic shielding member is formed of the above metal, these magnetic shielding members are desirably formed by, for example, press working or like plastic processing, whereby they can be formed more economically than in the case where the magnetic shielding member is formed by cutting or like means.

The fluid dynamic bearing apparatus mentioned above can be provided with a thrust bearing portion which freely rotatably supports the shaft member in the thrust direction. Various structures are possible for such a thrust bearing portion. For example, when the fixed-side member has a bearing sleeve with the shaft member inserted at its inner periphery and a housing comprising the bearing sleeve fixed thereinside and an opening portion on one end side and an integral or a separate bottom on the other end side, a structure in which a thrust bearing gap is proved between the opening portion of the housing and the rotational-side member (the member having a portion for mounting a rotor magnet) and the shaft member is supported in the thrust direction in a non-contact manner by the hydrodynamic effect of a fluid produced in this thrust bearing gap can be considered (refer to FIGS. 2, 5, 6 and 7).

Another possible example of the thrust bearing portion is that in which a thrust bearing gap is provided between the bottom of the housing and the shaft member and the shaft member is supported in the thrust direction in a non-contact manner by the hydrodynamic effect of a fluid produced in this thrust bearing gap (refer to FIG. 8).

Still another possible thrust bearing portion is that in which the shaft member is contactingly supported by housing. In this case, the shaft member contacts the bottom of the housing or other members constituting the bottom of the housing (such as a thrust plate, etc.) (refer to FIG. 9).

The fluid dynamic bearing apparatus which produces a series of these effects can be suitably provided as a motor constituted of this fluid dynamic bearing apparatus, a rotor magnet, a stator coil which produces excitation between itself and the rotor magnet.

As mentioned above, according to the fluid dynamic bearing apparatus of the present invention, since the rotational-side member is a molded resin article, the weight and cost of the rotational-side member can be reduced. Further, the rotational-side member is insert-molded together with the metal parts so that molding and assembly of the rotational-side member can be carried out in one step. Accordingly, the production cost of the motor can be reduced and at the same time molding precision and assembly precision of the rotational-side member can be increased. Moreover, by providing the magnetic shielding member, the leakage of the magnetic flux can be suppressed and the rotational performance of the motor can be increased.

DETAILED DESCRIPTION OF THE INVENTION

Embodiments of the present invention will be described below with reference to drawings.

Figure 1:
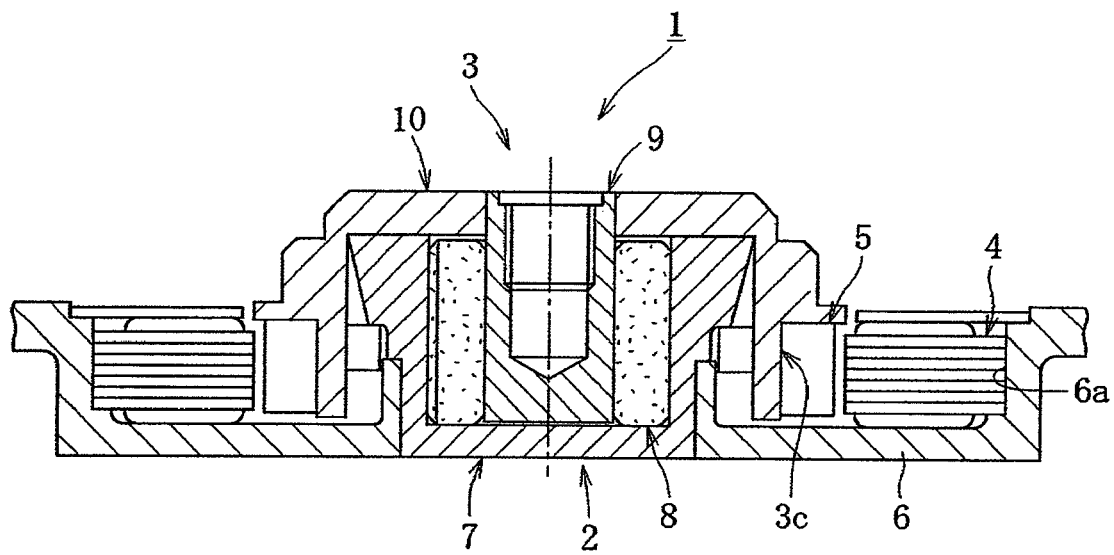
FIG. 1 is a cross-sectional view of a spindle motor information appliances integrating the fluid dynamic bearing apparatus according to the first embodiment of the present invention.

FIG. 1 shows a constitutional example of a spindle motor for information appliances incorporating a fluid dynamic bearing apparatus 1 according to a first embodiment of the present invention. This spindle motor for information appliances is for use in disk drive units such as HDD, and comprises a fluid dynamic bearing apparatus 1 having a fixed-side member 2 and having a rotational-side member 3 which is freely rotatable relative to the fixed-side member 2 and, for example, a stator coil 4 and a rotor magnet 5 which oppose each other across a gap in the radial direction, and a bracket 6. The stator coil 4 is attached on the inner side face 6$a$ of the bracket 6, and the rotor magnet 5 is attached on the outer periphery of the rotational-side member 3, more specifically on the outer periphery of a disk hub 10 which can retain one or a plurality of disk-shaped information recording media such as magnetic disks on its outer periphery. The housing 7 of the fluid dynamic bearing apparatus 1 is attached on the inner periphery of the bracket 6. When the stator coil 4 is energized, the rotor magnet 5 is rotated by the excitation produced between the stator coil 4 and rotor magnet 5, and accordingly the rotational-side member 3 rotates.

Figure 2:
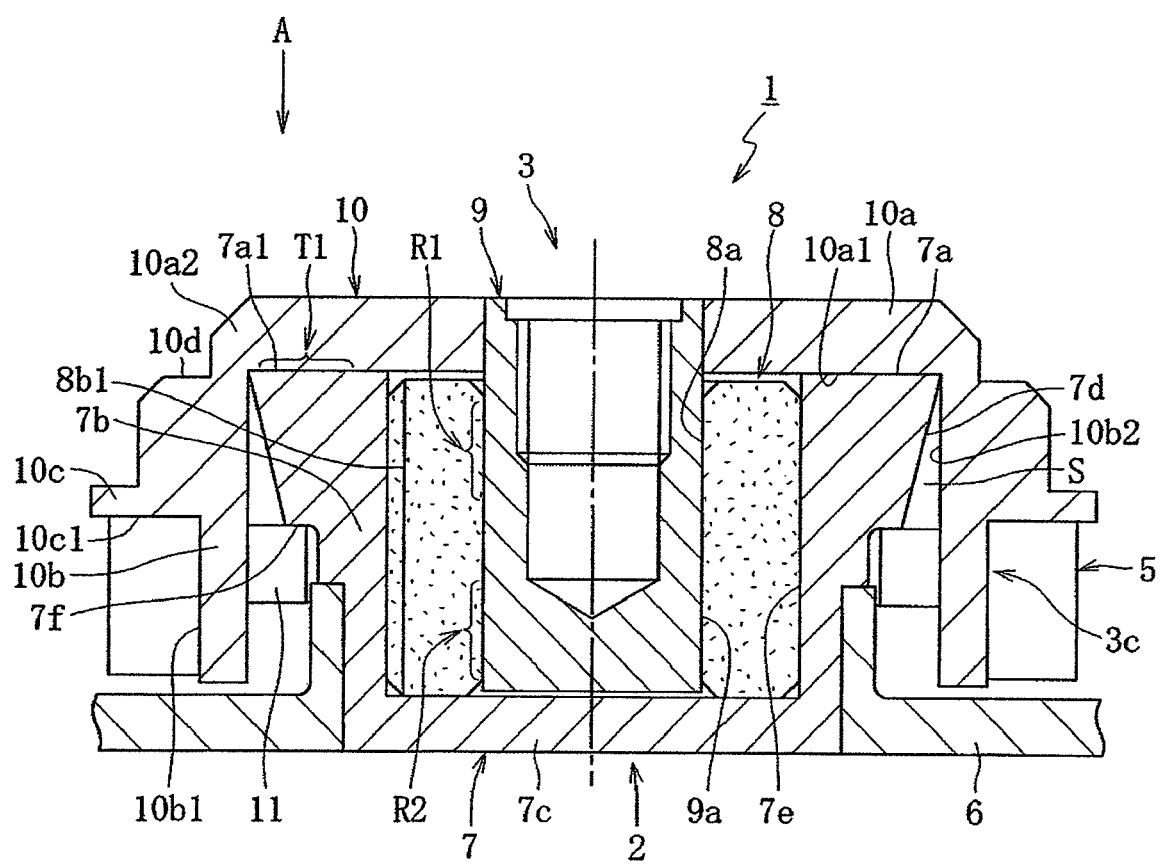
FIG. 2 is across-sectional view of the fluid dynamic bearing apparatus according to the first embodiment.

The fluid dynamic bearing apparatus 1 comprises a fixed-side member 2 and a rotational-side member 3. The fixed-side member 2 is, as shown in FIG. 2, for example, constituted mainly of the housing 7 and bearing sleeve 8, and the rotational-side member 3 is constituted mainly of a shaft member 9 and the disk hub 10.

The shaft member 9 is formed by, for example, cutting or forging a metallic material such as stainless steel, and is inserted at the inner periphery of the bearing sleeve 8. In a state that this shaft member 9 is inserted at the inner periphery of the bearing sleeve 8 and is rotated, between the inner circumferential surface 8$a$ of the bearing sleeve 8 and the outer circumferential surface 9$a$ of the shaft member 9, a first radial bearing portion R1 and a second radial bearing portion R2 are formed separately in the axial direction. Moreover, a thrust bearing portion T1 is formed between an end face 7$a$ of an opening portion of the housing 7 and an end face 10$a$1 on the lower end face of the disk hub 10. It should be noted that for the sake of explanation, the side of the end face 7$a$ of an opening portion of the housing 7 is referred to as the upper side, while the side opposite to the end face 7$a$ of the opening portion is referred to as the lower side in the description below.

Figure 3:
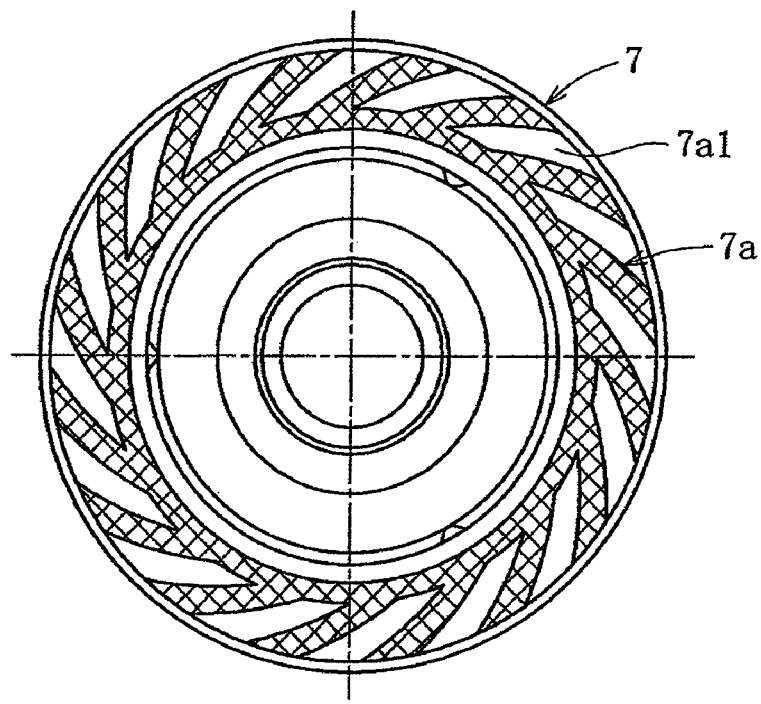
FIG. 3 is a drawing of a housing seen from the direction A in FIG. 2.
Figure 6:
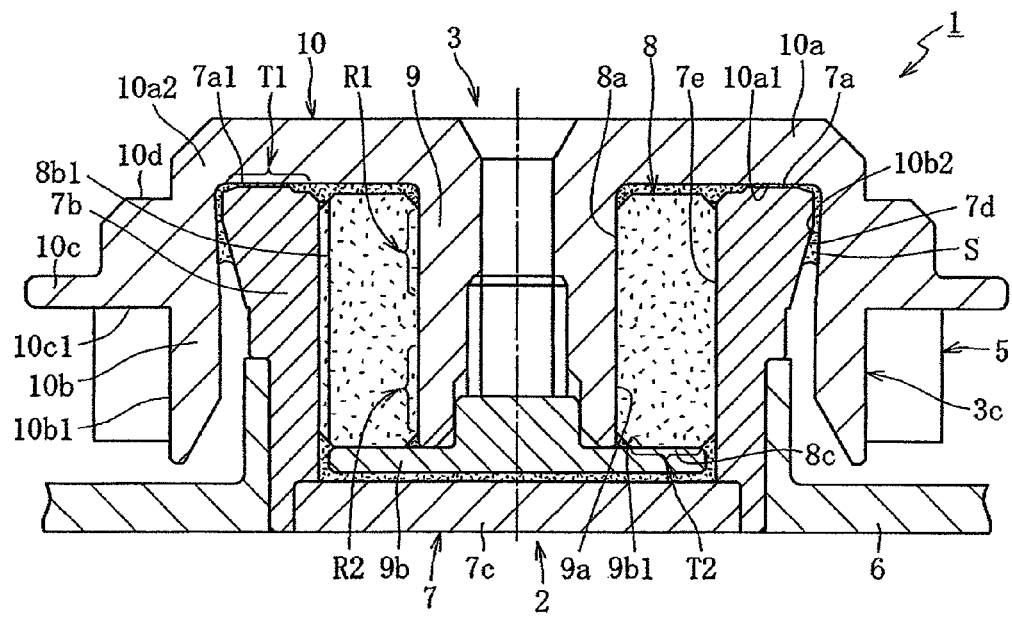
FIG. 6 is a cross-sectional view showing one variation example of the fluid dynamic bearing apparatus according to the first embodiment.

The housing 7 comprises a cylindrical side portion 7$b$, a bottom 7$c$ which is positioned at the lower end of the side portion 7$b$ and is integrated into or separated from the housing 7. The bottom 7$c$ in this embodiment is formed integrally with the side portion 7$b$, and, for example, is injection-molded of a resin composition based on a crystalline resin such as liquid crystal polymers, PPS, PEEK and like into a bottomed cylindrical shape. On the end face 7$a$ of the opening portion which serves as a thrust bearing face of the thrust bearing portion T1, for example, as shown in FIG. 3, a plurality of hydrodynamic grooves 7$a$1 having a spiral shape are formed. This hydrodynamic groove 7$a$1 is formed when the housing is molded. That is, a groove pattern for forming the hydrodynamic grooves 7$a$1 is preliminarily processed in a portion for forming the end face 7$a$ of the opening portion, of a mold which forms the housing 7, and the shape of the above groove pattern is transferred onto the end face 7$a$ of an opening portion of the housing 7 when the housing is molded, whereby the hydrodynamic grooves 7$a$1 can be formed simultaneously with the molding of the housing 7. The housing 7 comprises a tapering outer wall 7$d$ whose diameter gradually increases to the top on the upper outer periphery of the side portion 7$b$. It should be noted that in this embodiment, the bottom 7$c$ is, for example, formed integrally with the side portion 7$b$ by injection molding of the above resin material, but the bottom 7$c$ may be formed separately from the side portion 7$b$ and attached to the side portion 7$b$ later. In this case, as shown in FIG. 6, for example, the lower end of the shaft member 9 is provided with a flange portion 9$b$, and a thrust bearing portion T2 which supports the shaft member 9 in the thrust direction in a non-contact manner can be formed between the upper end face 9$b$1 of the flange portion 9$b$ and the lower end face 8$c$ of the bearing sleeve 8.

The bearing sleeve 8 can be formed, for example, of brass and like copper alloys and aluminum alloy and like metals, or can be formed of a porous body comprising a sintered metal. In this embodiment, it is formed of a porous body of a sintered metal comprising copper as a main ingredient in a cylindrical shape, and is fixed in a predetermined position of the inner circumferential surface 7$e$ of the housing 7.

Figure 4:
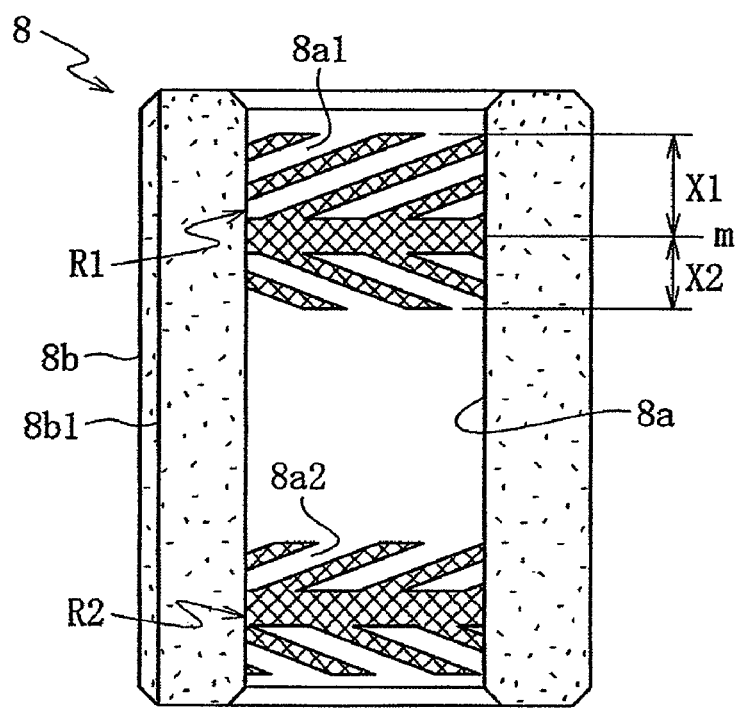
FIG. 4 is a cross-sectional view of a bearing sleeve.

On the inner circumferential surface 8$a$ of the bearing sleeve 8, upper and lower regions which serve as radial bearing faces of the first radial bearing portion R1 and second radial bearing portion R2 are provided separately in the axial direction. In these two regions, as shown in FIG. 4, for example, a plurality of hydrodynamic grooves 8$a$1, 8$a$2 are arranged each in a herringbone shape. The upper hydrodynamic grooves 8$a$1 are formed axially asymmetrically relative to the axial center m (the axial center of the region between the upper and lower slanted grooves), and the axial dimension X1 of the region above the axial center m is greater than the axial dimension X2 of the region therebelow. Moreover, one or a plurality of axial grooves 8$b$1 are formed on the outer circumferential surface 8$b$ of the bearing sleeve 8 throughout the axial length of the shaft. In this embodiment, three axial grooves 8$b$1 are formed at regular intervals in the circumferential direction.

The disk hub 10 comprises an approximately disk-shaped base 10$a$, a peripheral wall portion 10$b$ extending downwardly in the axial direction from the outer circumference 10$a$2 of the base 10$a$, a brim 10$c$ provided on the outer periphery of the peripheral wall portion 10$b$ and a disk loading face 10$d$. A mounting portion 3$c$ for attaching the rotor magnet 5 in this embodiment is constituted of the outer circumferential surface 10$b$1 of the peripheral wall portion 10$b$ of the disk hub 10 and a lower end face 10$c$1 of the brim 10$c$. On the outer circumferential surface 10$b$1 and lower end face 10$c$1, the rotor magnet 5 is fixed, for example, by adhesion or like means so that the rotor magnet 5 oppose the stator coil 4 (refer to FIG. 1) attached on the inner side face 6$a$ of the bracket 6 in the radial direction. Moreover, the inner circumferential surface 10$b$2 of the peripheral wall portion 10$b$ forms an annular sealing space S whose dimension in the radial direction gradually decreases from the side of the bottom 7$c$ of the housing 7 to the top between itself and the tapering outer wall 7$d$ of the housing 7. This sealing space S is in communication with the outer diameter side of the thrust bearing gap of the thrust bearing portion T1 while the shaft member 9 and disk hub 10 are in rotation. A slip-off prevention member 11 is fixed on the inner circumferential surface 10b2 of the peripheral wall portion 10b. This slip-off prevention member 11 engages a shoulder 7f formed on the outer periphery of the housing 7 in the axial direction, whereby the shaft member 9 and disk hub 10 are prevented from being pulled off upwardly.

The disk hub 10 of the above constitution is formed by injection-molding a resin material using the shaft member 9 of a metal which is previously formed by cutting, forging process or the like as an insert piece. By this insert molding, the disk hub 10 and shaft member 9 are integrated in a state that the upper end of the shaft member 9 is embedded at the center of the base 10a of the disk hub 10.

By forming the disk hub 10 integrally with the shaft member 9 by insert molding in this manner, molding of the disk hub 10 and mounting process of the disk hub 10 to the shaft member 9 can be carried out simultaneously. Therefore, the mounting process mentioned above can be dispensed with, and the assembly cost of the motor can be reduced. Moreover, when the disk hub 10 and shaft member 9 are integrally molded, using a high-precision mold to increase the positioning accuracy of the shaft member allows easily obtaining high mounting precision between the disk hub 10 and shaft member 9. Furthermore, the runout precision or coaxiality of the molded article can be maintained at a high level. Moreover, since the disk hub 10 is integrated in the shaft member 9 in a state that the shaft member 9 is partially embedded in the disk hub 10, a fixing force as high as or higher than in the case where it is fixed by adhesion, press fitting or like means can be obtained.

In addition to the shaft member 9, the rotor magnet 5 can be also used as an insert piece for insert-molding the disk hub 10. This can eliminate a mounting process of the rotor magnet 5 to the disk hub 10 and achieve greater cost reduction. Moreover, in this embodiment, hydrodynamic grooves 7a1 are formed on the end face 7a of the opening portion of the housing 7. However, for example, a groove pattern corresponding to the hydrodynamic grooves 7a1 can be processed in a portion of the disk hub 10 corresponding to the thrust bearing face a forming mold to form hydrodynamic grooves on the disk hub 10 simultaneously with the molding of the disk hub 10. In this case, since the hydrodynamic grooves of the thrust bearing face need not be formed separately, a greater cost reduction is enabled.

The bearing sleeve 8 is fixed in a predetermined position of the inner circumferential surface 7e of the housing 7 by, for example, adhesion (including loose adhesion, press fitting adhesion), press fitting, welding (including ultrasonic welding) or like fixing means. The shaft member 9 is inserted at the inner periphery of the bearing sleeve 8 fixed on the housing 7, and the disk hub 10 formed integrally with the shaft member 9 as stated above is integrated in the fixed-side member 2. The slip-off prevention member 11 is then fixed on the inner circumferential surface 10b2 of the peripheral wall portion 10b of the disk hub 10 attached on the bearing sleeve 8 by press fitting, adhesion or like means.

In the fluid dynamic bearing apparatus 1 of the above constitution, while the shaft member 9 (rotational-side member 3) is in rotation, a region which serves as the radial bearing faces of the inner circumferential surface 8a of the bearing sleeve 8 (a region in which upper and lower hydrodynamic grooves 8a1, 8a2 are formed) opposes the outer circumferential surface 9a of the shaft member 9 across the radial bearing gap. As the shaft member 9 rotates, the lubricating oil of the above radial bearing gap is pushed to the side of the axial center m of the hydrodynamic grooves 8a1, 8a2, and its pressure is increased. The first radial bearing portion R1 and the second radial bearing portion R2 which support the shaft member 9 (rotational-side member 3) in the radial direction in a non-contact manner are constituted by such hydrodynamic effect of the hydrodynamic grooves 8a1, 8a2.

Similarly, in the thrust bearing gap between the end face 7a of the opening portion of the housing 7 (region in which the hydrodynamic grooves 7a1 are formed) and the end face 10a1 on the lower side of the opposing disk hub 10, an oil film of the lubricating oil is formed by the hydrodynamic effect of the hydrodynamic grooves. The first thrust bearing portion T1 which supports the shaft member 9 (rotational-side member 3) in the thrust direction in a non-contact manner is constituted by this pressure of the oil film.

The first embodiment of the present invention is described above, but the present invention is not limited to this embodiment. Another constitutional example of the fluid dynamic bearing apparatus will be described below. It should be noted that in the drawings shown below, parts and components having the same constitutions and functions as in the first embodiment are referred to by the identical reference numerals, and their repeated description will be omitted.

Figure 5:
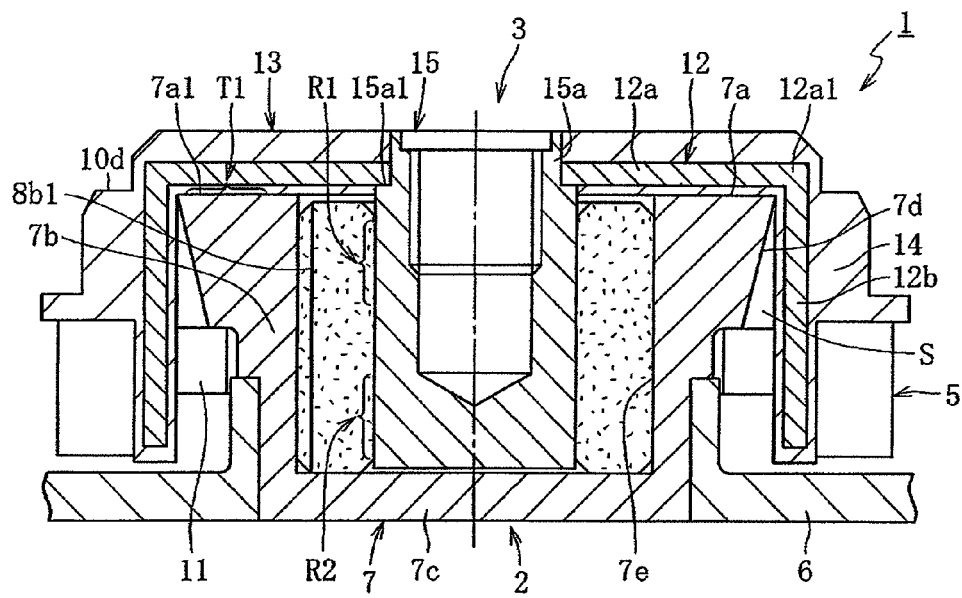
FIG. 5 is a cross-sectional view showing one variation example of the fluid dynamic bearing apparatus according to the first embodiment.

FIG. 5 shows a fluid dynamic bearing apparatus 1 according to a variation example of the first embodiment. A disk hub 13 in this fluid dynamic bearing apparatus 1 is, unlike in the first embodiment, a molded resin article in which a core 12 made of a metal is further integrated therein in addition to the shaft member 15. More specifically, the core 12 has such a shape that a ring-shaped peripheral wall portion 12b extends downwardly in the axial direction from the outer diameter side edge 12a1 of an approximately disk-shaped base 12a as well as the disk hub 13, and has a thickness nearly constant throughout its entire body. Both front and back faces of this core 12 and the tip of the peripheral wall portion 12b are covered with a resin portion 14. The disk hub 13 is, for example, insert-molded by injection-molding a resin material using the previously formed shaft member 15 and core 12 as insert pieces. By this insert molding, the disk hub 13 and shaft member 15 are integrated in a state that an upper end portion 15a of the shaft member 15 is embedded at the center of the base 12a and the core 12 is embedded throughout the entire disk hub 13.

By forming the disk hub 13 having the core 12 embedded throughout the entire disk hub 13 in this manner from a resin material, the weight and production cost of the disk hub 13 can be reduced, and at the same time a dimensional change during molding and during use can be reduced and molding dimensional accuracy of the disk hub 13 and thus of the rotational-side member 3 can be increased. In the disk hub 13, it is desirable that in a part where precision is particularly required, i.e., the mounting portion of the rotor magnet 5 in the illustrated example, the thickness of the resin portion 14 is the same on both front and back sides of the core 12.

Moreover, in this embodiment, a shoulder 15a1 is formed in the upper end portion 15a of the shaft member 15 embedded in the disk hub 13 of the shaft member 15, the core 12 exposed in the inner diameter portion of the disk hub 13 and the shaft member 15 are engaged in the axial direction at the shoulder 15a1. Therefore, the positioning accuracy of the core 12 relative to the shaft member 15 can increased, and therefore the mounting accuracy of the disk hub 13 to the shaft member 15 can be increased.

The core 12 can be formed, for example, of a magnetic substance such as stainless steel. According to this, the magnetic flux which may pass from the rotor magnet 5 to the inner diameter side via the disk hub 13 is blocked by the core 12. Therefore, the magnetic flux produced between the stator coil 4 and the rotor magnet 5 can be prevented from leaking. It should be noted that the core 12 can be die-formed, for example, by press working and like plastic processing to enable production at a lower cost.

In addition, the core 12 can be formed, for example, of a porous body such as a sintered metal. According to this, since the resin portion 14 around the core 12 is cured in a state that it bites into the pores on the surface of the porous body, a kind of anchor effect is produced to the core 12 and sticking strength between the resin portion 14 and the core 12 is further increased.

FIG. 5 shows an example in which the core 12 and the shaft member 15 are both insert pieces, but it is also possible that only the core 12 is an insert piece for constituting the disk hub 13 by insert-molding. In this case, the shaft member 15 is fixed to the disk hub 13 which has been molded by a suitable means such as adhesion and press fitting.

Figure 7:
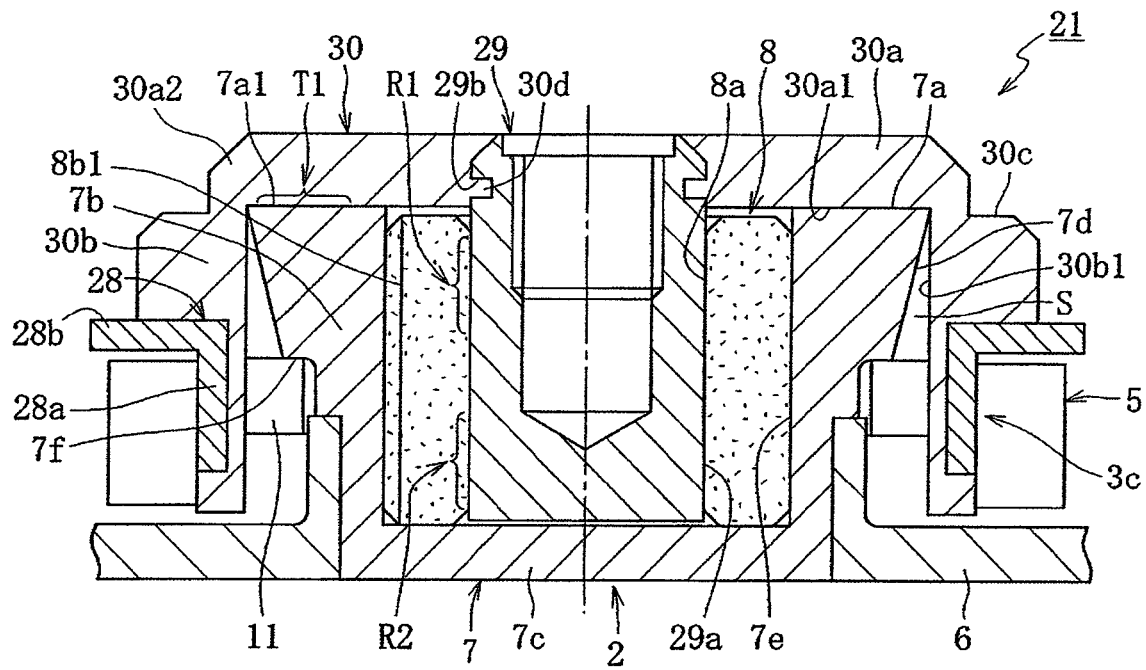
FIG. 7 is an enlarged sectional view of a spindle motor for information appliances integrating a fluid dynamic bearing apparatus according to a second embodiment of the present invention for information appliances.

FIG. 7 conceptionally and partially shows a constitutional example of a fluid dynamic bearing apparatus 21 according to a second embodiment of the present invention and of a spindle motor for information appliances integrating this fluid dynamic bearing apparatus 21. This spindle motor for information appliances is for use in disk drive units such as HDD, and comprises a fluid dynamic bearing apparatus 21 which freely rotatably supports a shaft member 29 by a fixed-side member 2, a stator coil 4 and a rotor magnet 5 which, for example, oppose each other across a gap in the radial direction (refer to FIG. 1) and a bracket 6. The rotor magnet 5 is attached on the outer periphery of a disk hub 30 as a member having a portion 3c for mounting the rotor magnet 5. This disk hub 30 retains one or a plurality of magnetic disks and like disk-shaped information recording media on its outer periphery. The housing 7 of the fluid dynamic bearing apparatus 21 is attached on the inner periphery of the bracket 6. When the stator coil 4 is energized, the rotor magnet 5 is rotated by the excitation produced between the stator coil 4 and rotor magnet 5, and the housing 7 as a fixed-side member 2 and a disk hub 30, and thus a shaft member 29 rotate relative to a bearing sleeve 8 accordingly.

The fluid dynamic bearing apparatus 21 in this drawing comprises the fixed-side member 2, the shaft member 29 which rotates relative to the fixed-side member 2, the disk hub 30 and a magnetic shielding member 28. In this embodiment, the parts on the rotation side (shaft member 29, disk hub 30, magnetic shielding member 28) will be mainly described.

The disk hub 30 as a member having the portion 3c for mounting the rotor magnet 5 is formed by injection-molding a resin composition based on a liquid crystal polymers, PPS, PEEK or like crystalline resins, as mentioned above. The disk hub 30 of this embodiment comprises an approximately disk-shaped base 30a, a peripheral wall portion 30b extending downwardly from the outer circumference 30a2 of the base 30a in the axial direction and a disk loading face 30c provided on the outer periphery of the peripheral wall portion 30b. The disk-shaped information recording media, which are not shown, are mounted on the disk loading face 30c, and are retained on the disk hub 30 by an appropriate retaining means, which is not shown. A magnetic shielding member 28 is attached to a lower end portion of the peripheral wall portion 30b integrally with the disk hub 30.

The magnetic shielding member 28 is molded, for example, by plastic processing (press working, etc.) of a metal plate comprising a ferromagnetic substance such as martensite-based stainless steel or ferrite-based stainless steel. The magnetic shielding member 28 in this embodiment has an approximately L shape in cross section, and comprises an axial direction portion 28a extending along the peripheral wall portion 30b in the axial direction and a radial direction portion 28b extending from the upper end of the axial direction portion 28a to the outer diameter side. Of course, metallic materials other than stainless steel mentioned above, oxides of these metals, ceramics and other materials can be used for the magnetic shielding member as materials as long as they are magnetic materials.

As mentioned above, the rotor magnet 5 is attached to the mounting portion 3c of the disk hub 30 by adhesion or like means. In this embodiment, the outer periphery (the outer periphery of the axial direction portion 28a) of the magnetic shielding member 28 provided in the peripheral wall portion 30b of the disk hub 30 is used as the mounting portion 3c and the rotor magnet 5 is fixed by adhesion directly to this mounting portion 3c to realize metal adhesion and improve the fixing force.

The disk hub 30 of the above constitution is molded by injection-molding a resin material using the shaft member 29 which is previously molded and magnetic shielding member 28 as insert pieces (insert molding). By this insert molding, the disk hub 30 and shaft member 29 are integrated in a state that the upper end of the shaft member 29 is embedded at the center of the base 30a of the disk hub 30, and the disk hub 30 and magnetic shielding member 28 are integrated in a state that the magnetic shielding member 28 is embedded in the outer periphery of the peripheral wall portion 30b of the disk hub 30. In the upper end portion of the shaft member 29, a groove 29b is formed in the radial direction as a slip-off prevention for the disk hub 30 in the axial direction.

The disk hub 30 is molded integrally with the shaft member 29 and magnetic shielding member 28 by insert molding in this manner, whereby the molding of the disk hub 30 and the mounting processes of the disk hub 30, shaft member 29 and magnetic shielding member 28 can be carried out simultaneously, and the assembling of the motor can be reduced. Moreover, in the insert molding, the positioning accuracy of the shaft member 29 and magnetic shielding member 28 is increased by using a high-precision mold, thereby easily obtaining high mounting accuracy and maintaining the runout precision and coaxiality of the molded article at a high level. The rotor magnet 5 can be further used as an insert piece in addition to the shaft member 29 and magnetic shielding member 28 for injection-molding the disk hub 30.

Moreover, in the present invention the magnetic shielding member 28 which functions as a magnetic shielding is disposed in a portion which opposes the rotor magnet 5 in the disk hub 30. Leakage of the magnetic flux which acts between the rotor magnet 5 and stator coil 4 via the disk hub 30 can be prevented. Therefore, the magnetic flux density between the rotor magnet 5 and the stator coil 4 opposing the rotor magnet 5 can be increased and the rotational performance of the can be improved.

In order to prevent flux leakage, it is desirable that all the region other than a portion of the rotor magnet 5 which opposes the stator coil 4 is coated by the magnetic shielding member 28, but in this embodiment, considering the processability and other properties of the magnetic shielding member 28, the magnetic shielding member 28 is provided with an axial direction portion 28a and the radial direction portion 28b to shield magnetism mainly at the inner diameter side and upper side of the rotor magnet 5. Of course, the shape of the magnetic shielding member 28 can be appropriately changed to shield the magnetism on another side (for example, lower side), or to limit the direction of the magnetic shielding (for example, magnetism is shielded only at the inner diameter side).

Moreover in this embodiment, as shown in FIG. 7, the magnetic shielding member 28 and the disk hub 30 are molded integrally in a manner of adhering the magnetic shielding member 28 to the outer periphery of the disk hub 30 and the outer circumferential surface of the magnetic shielding member 28 is exposed. However, part or the entire magnetic shielding member 28 may be embedded in part of the disk hub 30. In this case, since a portion of the magnetic shielding member 28 which is embedded in the resin portion is bound by the shrinkage caused when a molten resin is cured from both sides, the sticking strength of the magnetic shielding member 28 can be increased.

In the fluid dynamic bearing apparatus 1 of the above-mentioned constitution, while the shaft member 29 (disk hub 30) is in rotation, regions which serve as radial bearing faces of the inner circumferential surface 8a of the bearing sleeve 8 (regions in which upper and lower hydrodynamic grooves 8a1, 8a2 are formed) oppose the outer circumferential surface 29a of the shaft member 29 across the radial bearing gap. As the shaft member 29 rotates, the lubricating oil in the above radial bearing gap is pushed toward the side of the axial center m of the hydrodynamic grooves 8a1, 8a2 (refer to FIG. 4), and its pressure increases. By such hydrodynamic effect of the hydrodynamic grooves 8a1, 8a2, a first radial bearing portion R1 and a second radial bearing portion R2 which support the shaft member 29 (disk hub 30) in the radial direction in a non-contact manner are constituted respectively.

Similarly, in the thrust bearing gap between the end face 7a of the opening portion of the housing 7 (region in which the hydrodynamic grooves 7a1 are formed) and an opposing lower end face 30a1 of the disk hub 30, an oil film of the lubricating oil is formed by the hydrodynamic effect of the hydrodynamic grooves. By this pressure of the oil film, a first thrust bearing portion T1 which supports the shaft member 29 (disk hub 30) in the thrust direction in a non-contact manner is constituted.

FIG. 7 (FIG. 1) shows a motor in which the stator coil 4 is disposed on the inner diameter side and the rotor magnet 5 is disposed on the outer diameter side as an example, but in contrast, the present invention can be also applied to a motor in which the rotor magnet 5 is disposed on the inner diameter side and the stator coil 4 is disposed on the outer diameter side. Moreover, this Fig. shows a radial gap motor in which a gap in the radial direction is provided between the stator coil 4 and rotor magnet 5, but the present invention can be also applied to an axial gap motor in which a gap is provided in the axial direction between the stator coil 4 and rotor magnet similarly.

Figure 8:
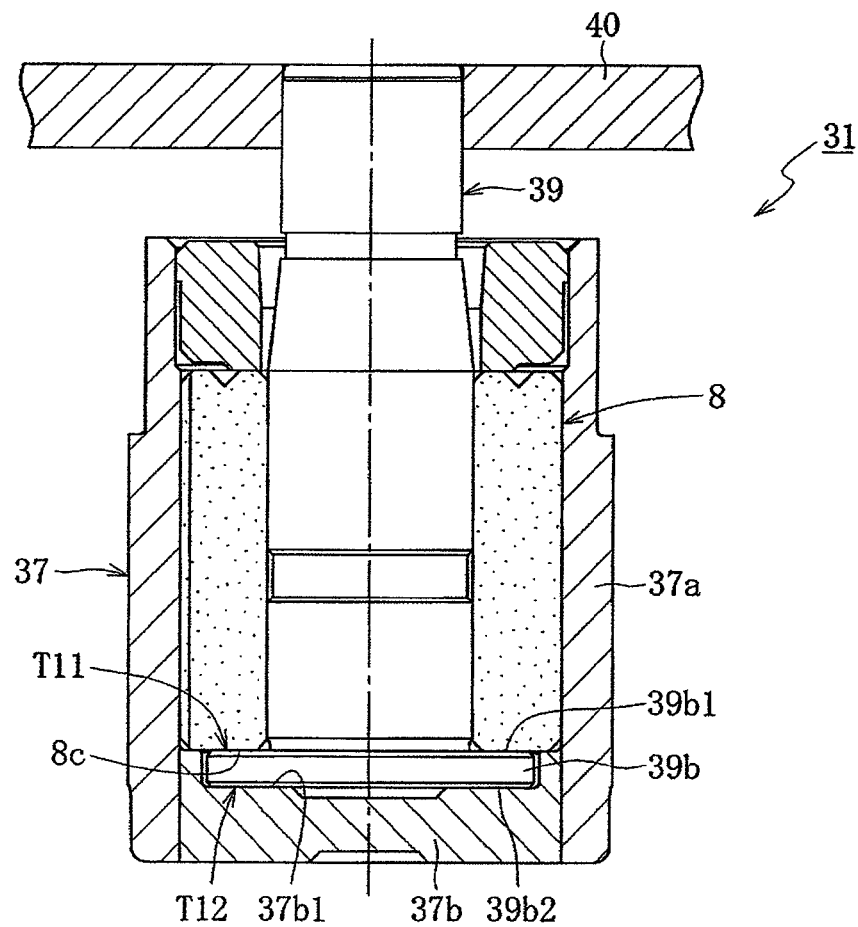
FIG. 8 is an enlarged sectional view of a spindle motor for information appliances integrating a fluid dynamic bearing apparatus according to the third embodiment of the present invention.

FIG. 8 is an enlarged sectional view of a spindle motor for information appliances integrating a fluid dynamic bearing apparatus 31 according to a third embodiment of the present invention. A thrust bearing gap is formed between the housing 7 and disk hub 10 (30) in the first and second embodiments, while in contrast, a thrust bearing gap is formed between the housing 37 and shaft member 39, and between the bearing sleeve 8 and shaft member 39, respectively, in this embodiment. This embodiment is different from the above-mentioned embodiments in this term. Specifically, the shaft member 39 comprises a flange portion 39b provided integrally or separately at its lower end. Moreover, a bottom 37b positioned in a lower end portion of the housing 37 is formed separately from a side portion 37a of the housing 37, and is retrofitted to the side portion 37a. On the inner bottom face 37b1 of this bottom 37b, although not illustrated, for example, hydrodynamic grooves having the same shape as in FIG. 3 are formed, and hydrodynamic grooves having a similar shape (having the opposite spiral direction) are formed on the lower end face 28c of the bearing sleeve 8. In a state that the above shaft member 39 is inserted at the inner periphery of the bearing sleeve 8 and rotated, a thrust bearing gap is formed between the lower end face 8c of the bearing sleeve 8 and a upper end face 39b1 of the flange portion 39b of the shaft member 39, and hydrodynamic effect of the lubricating oil is produced in this thrust bearing gap, thereby forming a first thrust bearing portion T11 which supports the shaft member 39 in the thrust direction in a non-contact manner. Simultaneously, a thrust bearing gap is also formed between the inner bottom face 37b1 of the bottom 37b attached to a lower end portion of the housing 37 and the lower end face 39b2 of the flange portion 39b. The hydrodynamic effect produced of the lubricating oil in this thrust bearing gap forms a second thrust bearing portion T12 which supports the shaft member 39 in the thrust direction in a non-contact manner.

In this embodiment, the disk hub 40 which retains magnetic disks and like disks is insert-molded by injection molding a resin material using the shaft member 39 previously formed by forging or other means as an insert piece, and, although not illustrated, the magnetic shielding member stated above as an insert piece. In this case, the rotor magnet is attached to a mounting portion of the rotor magnet of the disk hub 40, although not illustrated either, and the magnetic shielding member is installed in a position which opposes the rotor magnet in the disk hub 40. By this insert molding, the disk hub 40, shaft member 39 and magnetic shielding member are integrated in a state that the shaft member 39 passes through the center of the disk hub 40.

As mentioned above, also in the third embodiment, the disk hub 30 is molded integrally with the shaft member 29 by insert molding, whereby the process of mounting of the disk hub 30 to the shaft member 29 can be dispensed with and the cost of assembling the motor can be reduced. Furthermore, high mounting precision between the disk hub 30 and shaft member 29 can be obtained so that sufficient fixing force between them can be ensured. Moreover, a magnetic shielding member is disposed in a position in the disk hub 40 which opposes the rotor magnet, whereby magnetic flux leakage from the rotor magnet can be suppressed. Furthermore, the disk hub 40 can be insert-molded with the core as in the variation example shown in FIG. 5 also in this embodiment, and accordingly the molding dimensional accuracy of the disk hub 40 can be increased.

Figure 9:
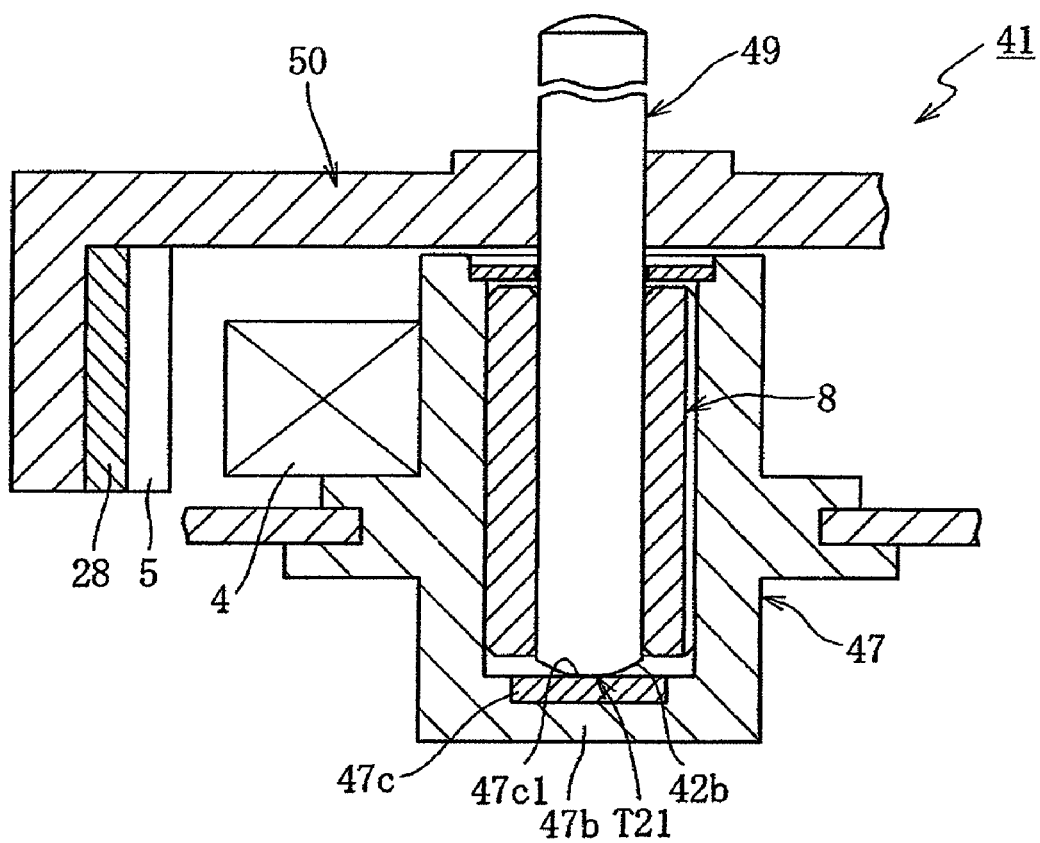
FIG. 9 is an enlarged sectional view of a polygon scanner motor integrating a fluid dynamic bearing apparatus according to the fourth embodiment of the present invention.

FIG. 9 is an enlarged sectional view of a polygon scanner motor integrating a fluid dynamic bearing apparatus 41 according to a fourth embodiment. This embodiment is different from the first to third embodiments in that the thrust bearing portion T21 is not a non-contact type fluid dynamic bearing but a contact type pivot bearing. Specifically, the shaft member 49 has a shaft-like shape without a flange portion, and its lower end 49b is formed in a convex sphere shape. The shaft member 49 is contactingly supported with its lower end 49b in pivot contact with the inner bottom face 47c1 of a thrust washer 47c fixed on the housing 47 in the thrust direction.

At this time, for example, the rotor member 50 as a member having a polygon mirror attached thereto and a portion for mounting a rotor magnet is insert-molded by injection molding or like means of a resin material using the shaft member 49 which is previously molded as an insert piece and, the magnetic shielding member stated above although not illustrated, as an insert piece. In this case, the rotor magnet is attached to the portion for mounting the rotor magnet in the rotor member 50, although not illustrated either, and the magnetic shielding member is installed in a position opposing the rotor magnet in the rotor member 50. By this insert molding, the rotor member 50, shaft member 49 and magnetic shielding member are integrated in a state that the shaft member 49 passes through the center of the rotor member 50.

As mentioned above, also in the fourth embodiment, as in the first to third embodiments, the rotor member 50 is formed integrally with the shaft member 49 by insert molding, whereby the process of mounting the rotor member 50 to the shaft member 49 can be dispensed with, and the cost of assembling the motor can be reduced. Moreover, magnetic flux leakage from the rotor magnet can be suppressed by disposing a magnetic shielding member in a position in the rotor member 50 which opposes the rotor magnet. Of course in this embodiment, the rotor member 50 can be insert-molded integrally with the core, and molding dimensional accuracy of the rotor member 50 can be increased as in the above first to third embodiments.

The first to fourth embodiments mentioned above describe the case where a plurality of hydrodynamic grooves 8a1, 8a2 are provide as a hydrodynamic pressure producing means for producing the hydrodynamic effect of a fluid in the radial bearing gap of the radial bearing portions R1, R2, but other forms may be also employed. For example, although not illustrated, it is possible to employ a so-called stepped hydrodynamic pressure producing part which has grooves in the axial direction are formed in a plurality of positions in the circumferential direction or a so-called multilobe bearing in which a plurality of arcuate faces are arranged in the circumferential direction and a radial-direction gap (bearing gap) having a wedge shape is formed between these faces and the opposing outer circumferential surface 9a of the shaft member 9.

Moreover, one or both of the thrust bearing portions T1, T2 (T11, T12) may be constituted of a so-called step bearing in which a plurality of hydrodynamic grooves in a radial groove shape are provided in a region which serves as a thrust bearing face, at predetermined intervals in the circumferential direction, or a wave bearing (having a wave shape instead of the steps) or like bearings, although not illustrated either.

Moreover, the above embodiments describe the cases where the radial bearing face is formed on the side of the bearing sleeve 8, while the hydrodynamic pressure producing part is formed on the side of the housing 7, 37. However, the face where these hydrodynamic pressure producing parts are formed is not limited to those of the parts on the fixed side, and can be, for example, the side of the shaft member 9 and flange portion 9b, 39b opposing these parts, or on the side of the disk hub 10, 13, 30 (rotation side).

INDUSTRIAL APPLICABILITY

This fluid dynamic bearing apparatus is suitable for spindle motors for information appliances, for example, HDD and like magnetic disk apparatuses, CD-ROM, CD-R/RW, DVD-ROM/RAM and like optical disk apparatuses, MD, MO and like magneto-optic disk apparatuses, polygon scanner motors of laser beam printers (LBP) or small motors for axial fans and the like.

The invention claimed is:
1. A fluid dynamic bearing apparatus comprising:
a shaft member;
a fixed-side member which freely rotatably supports the shaft member;
a member which is attached to the shaft member and has a portion for mounting a rotor magnet; and
a magnetic shielding member,
wherein the shaft member is supported in a radial direction in a non-contact manner by a hydrodynamic effect of a fluid which is produced in an annular radial bearing gap between the fixed-side member and the shaft member,
wherein the member having the portion for mounting the rotor magnet is formed of a resin,
wherein the magnetic shielding member comprises a magnetic substance and has an approximate L-shape in cross section, the magnetic shielding member including an axial direction portion extending in an axial direction and a radial direction portion extending in the radial direction from an end portion of the axial direction portion, the axial direction portion and the radial direction portion being formed integrally with each other, the magnetic shielding member being disposed in the member having the portion for mounting the rotor magnet, and wherein the rotor magnet is fixed to an outer periphery of the axial direction portion of the magnetic shielding member so as to oppose the radial direction portion of the magnetic shielding member.

2. A fluid dynamic bearing apparatus according to claim 1, wherein the member having the portion for mounting the rotor magnet is an injection-molded article of a resin using the magnetic shielding member as an insert piece.

3. A fluid dynamic bearing apparatus according to claim 1, wherein at least part of the magnetic shielding member is embedded in the resin.

4. A fluid dynamic bearing apparatus according to claim 1, wherein the magnetic shielding member is formed by plastic processing.

5. A fluid dynamic bearing apparatus according to claim 1, wherein the member having the portion for mounting the rotor magnet is an injection-molded article of a resin using the magnetic shielding member and the shaft member as insert pieces.

6. A fluid dynamic bearing apparatus according to claim 1, wherein the fixed-side member comprises a bearing sleeve into which the shaft member can be inserted at an inner periphery of the bearing sleeve, and a housing having the bearing sleeve fixed thereinside, the housing having an opening portion on one end side thereof and an integral or a separate bottom on the other end side thereof.

7. A fluid dynamic bearing apparatus according to claim 6, wherein a thrust bearing gap is provided between the opening portion of the housing and the member having the portion for mounting the rotor magnet, and the shaft member is supported in a thrust direction in a non-contact manner by the hydrodynamic effect of a fluid produced in the thrust bearing gap.

8. A fluid dynamic bearing apparatus according to claim 6, wherein a thrust bearing gap is provided between a bottom of the housing and the shaft member, and the shaft member is supported in a thrust direction in a non-contact manner by the hydrodynamic effect of a fluid produced in the thrust bearing gap.

9. A fluid dynamic bearing apparatus according to claim 6, wherein the shaft member is contactingly supported by the housing.

10. A motor comprising:
a fluid dynamic bearing apparatus according to claim 1;
a rotor magnet; and
a stator coil which produces excitation between itself and the rotor magnet.

11. A fluid dynamic bearing apparatus according to claim 1, wherein the radial direction portion of the magnetic shielding member extends radially outwardly from the end portion of the axial direction portion of the magnetic shielding member.

12. A fluid dynamic bearing apparatus according to claim 1, wherein the rotor magnet is spaced apart from the radial direction portion of the magnetic shielding member in the axial direction.

* * * * *